US009468653B2

(12) United States Patent
Fernandez

(10) Patent No.: US 9,468,653 B2
(45) Date of Patent: Oct. 18, 2016

(54) METHOD BASED ON BISMUTH ION FOR THE TREATMENT AND PREVENTION OF A DISEASE CAUSED BY A SHIGA TOXIN

(75) Inventor: Hector Manuel Fernandez, Buenos Aires (AR)

(73) Assignee: Soubeiran Chobet, Buenos Aires (AR)

( * ) Notice: Subject to any disclaimer, the term of this patent is extended or adjusted under 35 U.S.C. 154(b) by 0 days.

(21) Appl. No.: 13/503,818

(22) PCT Filed: Oct. 10, 2011

(86) PCT No.: PCT/IB2011/002377
§ 371 (c)(1),
(2), (4) Date: May 31, 2012

(87) PCT Pub. No.: WO2013/054148
PCT Pub. Date: Apr. 18, 2013

(65) Prior Publication Data
US 2014/0205682 A1    Jul. 24, 2014

(51) Int. Cl.
*A61K 33/24* (2006.01)
*A61K 31/29* (2006.01)
*A61K 31/618* (2006.01)

(52) U.S. Cl.
CPC ............ *A61K 33/245* (2013.01); *A61K 31/29* (2013.01); *A61K 31/618* (2013.01)

(58) Field of Classification Search
CPC combination set(s) only.
See application file for complete search history.

(56) References Cited

U.S. PATENT DOCUMENTS

| 6,248,371 | B1 | 6/2001 | Domenico | |
| 2008/0312429 | A1* | 12/2008 | Ling et al. | 536/55.1 |
| 2014/0127324 | A1* | 5/2014 | Linstedt et al. | 424/639 |

FOREIGN PATENT DOCUMENTS

WO    2008073517    6/2008

OTHER PUBLICATIONS

Sublis et al., (P-215) The inhibitory effect of Colloidal Bismuth Hydroxide Gel on enteropathogens and on the activity of Shiga toxins in *Escherichia coli* O157:H7, VTEC 2012, May 6-9, 2012.*
Bitzan, "Treatment Options for HUS Secondary to *Escherichia coli* 0157:H7." International Society of Nephrology (2009), vol. 75, No. 112, 62-66.
Casburn-Jones, et al. "Management of Infectious Diarrhoea." Gut (2004), 53: 296-305.
Gadewar, et al. "Current Concepts in the Evaluation, Diagnosis and Management of Acute Infectious Diarrhea." Current Opinion in Pharmacology (2005), 5: 559-565.
Scheiring, et al. "Treatment and Outcome of Shiga-Toxin-Associated Hemolytic Uremic Syndrome (HUS)." Journel of the International Pediatric Nephrology Association (2008), 23: 1749-1760.

* cited by examiner

*Primary Examiner* — Michael G Hartley
*Assistant Examiner* — Robert Cabral

(57) ABSTRACT

The present invention relates to the a bismuth-based composition, particularly involving the use of bismuth ions, particularly the $Bi^{+3}$ ion, for prevention and/or treatment of the haemolytic uremic syndrome, with the invention also relating to the use of a bismuth ion in the manufacture of a medicament for the prevention and/or treatment of an infection caused by a Shiga-toxin producing *Escherichia coli* strain, as well as to a method for preventing and/or treating the haemolytic uremic syndrome comprising administering bismuth ions to a patient in need thereof, and a method for inhibiting dissemination of the gene encoding virulence factors of a Shiga-toxin producing *Escherichia coli* strain in animals and humans.

8 Claims, No Drawings

METHOD BASED ON BISMUTH ION FOR THE TREATMENT AND PREVENTION OF A DISEASE CAUSED BY A SHIGA TOXIN

CROSS REFERENCE TO RELATED APPLICATIONS

This application is the United States National Stage of International Application No. PCT/IB2011/002377, filed Oct. 10, 2011. This application is incorporated by reference in its entirety herewith.

The present invention relates to the use of bismuth ions, particularly the $Bi^{+3}$ ion, in a composition and method of treatment for preventing and/or treating the haemolytic uremic syndrome. Furthermore, the invention is directed to the use of bismuth ions in the manufacture of a medicament for preventing and/or treating an infection caused by one or more Shiga toxin-producing *Escherichia coli* strains (for example, one or more strains selected from *Escherichia coli* O157:H7, 026:H11, O103:h2, O104:H4, O111:NM, O121:H19, and O145:NM). The invention is also directed to a method for the prevention and/or treatment of the haemolytic uremic syndrome comprising administering bismuth ions to a patient in need thereof. In addition, it also relates to a method for preventing *Escherichia coli* strains, producers of Shiga toxins, from disseminating in humans and animals.

BACKGROUND OF THE INVENTION

Infection by Shiga toxin-producing *Escherichia coli* (STEC) has been associated with enteric diseases since 1983, when Riley et al. reported the isolation of *Escherichia coli* O157:H7 in patients with haemorrhagic colitis associated with ingestion of undercooked hamburgers (*J Clin Microbiol* 1983; 18 (3): 512-20). That same year, Karmali et al. reported an association between STEC infection and haemolytic uremic syndrome (HUS) (*J Infect Dis* 1985; 151 (5): 775-82). Tests carried out in animal models as well as in vitro describe different virulence mechanisms. However, it has been proposed that the most important mechanism is the production of a potent cytotoxin, encoded by a bacteriophage, designated Shiga toxin (Stx). Human, animal or food STEC strains may produce Stx1, Stx2 or variants of Stx1 or Stx2, alone or as a combination of two or more toxins (Stx1/Stx2, Stx1/Stx2v, Stx1c/Stx2, Stx1c/Stx2d, Stx2/Stx2v) (Strockbine et al., *Infect. Immun.* 1986; 53: 135-40; Friedrich et al., *J. Clin. Microbiol.* 2003; 41: 2448-53).

The amino acid sequence of Stx1 is identical to that of *Shigella dysenteriae* Shiga toxin and Stx2 shows 58% sequence homology to Stx1. They carry a 60 MDa plasmid (po157), involved in the expression of adherence fimbria (EHEC fimbria) and an RTX toxin designated EHEC entero-haemolysin (EHEC-Hly), which is associated with severe disease in humans (Schmidt H. et al., 1995; *Infect Immun* 1995; 63 (3): 1055-61). It has been suggested that a protease encoded by this plasmid (EspP) would act as an additional virulence factor.

Like enteropathogenic *E. coli*, STEC carries a chromosomal gene designated eae encoding a protein designated intimin. This protein would be responsible of an intimate attachment of the bacteria to enterocytes and disorganization of microvilli, with production of an A/E lesion (attachment and effacement). Strains carrying the intimin gene and producing Stx2, are associated to severe disease in humans.

An infection by Shiga toxin-producing *Escherichia coli* is not only characterized by its aggressiveness and virulence, but is also responsible for severe enteric diseases in humans. It produces bloody diarrhea, and serious complications thereof may cause blood, renal and even brain cell damage leading to HUS. The toxins cause damage on the large intestine mucous lining and, if absorbed into the bloodstream, may affect other organs, such as kidneys.

The haemolytic uremic syndrome (HUS) is a generalized thrombotic microangiopathy, mainly accompanied by haemolytic anemia and varying degrees of renal failure. Currently, acute stage mortality ranges from 2.5 to 4%. Of all children affected, 55% become cured, 5% never regain normal renal function, suffering from different degrees of proteinuria and/or arterial hypertension, and the remaining 35% evolves to chronicity, after varying time periods.

At present, the treatment of HUS is symptomatic, consisting in early diagnosis, and usually involving the use of plasmapheresis, dialysis or haemodialysis in case of renal failure. Also, blood transfusions may be necessary in patients with severe anemia and intensive care in critically ill patients.

The American Academy of Pediatrics does not recommend the use of antibiotics and/or anti-diarrheal drugs which inhibit gastric motility, such as loperamide, in infants and children suspected of suffering from infectious gastroenteritis. (In: Pickering L K, ed. Red Book Report of the Committee on Infectious Diseases, $25^{th}$ ed., Elk Grove Village, 2000).

Previous studies have shown that treatment with antibiotics of an ECEH infection could significantly increase the risk of developing HUS. Bacterial membrane injuries, produced by antibiotics could increase massive release of preformed toxin. In addition, the use of antibiotics might bring about a selective advantage for ECEH over other bacteria which are less resistant to antibiotic therapy, thereby promoting ECEH proliferation.

It has also been demonstrated that certain antibiotics are potent inducers of Shiga toxin gene expression and may cause an increased toxin level in the intestine. Also, STEC strains have shown resistance to third generation cephalosporins and other antibiotics, such as Trimethoprim-Sulfa and Tetracyclines, in addition to being producers of broad-spectrum Beta-lactamases.

Infections by Shiga toxin-producing *Escherichia coli* strains, a food-borne pathogen in industrialized countries, are the main cause of the high incidence of HUS in Argentine children under 5 years of age.

Argentina has the highest rate of HUS incidence in the world (about 12.5 cases per 100,000 children under 5 years of age), with about 400 new cases per year, which represents the second cause of chronic renal failure (CRF) and of renal transplant indications in our country.

In its update of Jun. 6, 2011, the World Health Organization (WHO) reported the following cases in Germany:
630 HUS cases, 15 of them fatal.
1601 cases of diarrhea caused by enterohaemorrhagic *Escherichia coli* (ECEH), 6 of them fatal.
Furthermore, it was reported that the infection spread from Germany to 13 countries, including 12 European Union countries.

Several studies have demonstrated that the infection is foodborne, being bovine faeces the most common source of contamination. The infecting dose is very small, of about 102 CFU. Transmission is by food and water contaminated with bovine faeces and from person to person. US experience shows that lowering contamination of meat during slaughter it is not enough. The latest outbreak vectors have been vegetables contaminated with O157:H7, probably through fertilizers or irrigation water contaminated with bovine faeces. Contact of children with farm animals has also been recognized as a risk factor. All these evidences further support the need of reducing STEC excretion in the pre-slaughter stage.

Appropriate management practices would prevent spreading of pathogenic bacteria among cattle on a farm. It should be kept in mind that while some STEC strains are pathogenic for calves, most of them, including O157:H7, are zoonotic agents which do not affect the health of herds. Preventative measures would thus arise from the need of protecting public health and improving productivity.

Thus, to this date there is no method available for health professionals to prevent and/or treat haemolytic uremic syndrome (HUS).

BRIEF DESCRIPTION OF THE INVENTION

The present invention relates to the use of bismuth ions, in particular the $Bi^{+3}$ ion, in the manufacture of a medicament for the prevention and/or treatment of the haemolytic uremic syndrome and, particularly, for preventing and/or treating infections caused by Shiga toxin-producing *Escherichia coli* strains. Preferably, the medicament is for oral administration. Furthermore, the invention relates to a method for preventing and/or treating the haemolytic uremic syndrome comprising administering bismuth ions to a patient in need thereof. Moreover, the invention relates to the use of Bismuth ions in the manufacture of a medicament for inhibiting dissemination of the gene encoding virulence factors in Shiga toxin-producing *Escherichia coli* strains in humans and animals.

According to another object of the invention, a composition for preventing and/or treating the haemolytic uremic syndrome, is provided, wherein the composition comprises a bismuth ion.

It is still another object of the invention to provide a composition for preventing and/or treating an infection caused by one or more strains of Shiga toxin-producing *Escherichia coli*.

It is even another object of the invention to provide a method for preventing and/or treating a disease caused by at least one Shiga toxin, the method comprising administering a bismuth ion to a patient in need thereof.

It is another object of the invention to provide a method for preventing and/or treating a disease caused by at least one strain of Shiga toxin-producing *Escherichia coli*, the method comprising administering a bismuth ion to a patient in need thereof.

It is still another object of the invention to provide a method for preventing and/or treating the haemolytic uremic syndrome, the method comprising administering a bismuth ion to a patient in need thereof.

DETAILED DESCRIPTION OF THE INVENTION

Surprisingly, the present inventors have found that Bismuth ions, particularly $Bi^{+3}$ ions, are effective in suppressing virulence factors of Shiga-toxigenic *Escherichia coli* causing bloody diarrhea and HUS.

The present inventors have investigated the effect of Bismuth ions on the major pathogenic factors of Shiga toxin-producing *E. coli*, including Shiga toxins and lysogenic bacteriophages encoding Shiga toxins. Unexpectedly, they found that bismuth ions effectively inhibit the activity of Shiga toxins and cause a decrease in the titers of isolated Shiga toxin-encoding phages.

The present invention is directed to a method using bismuth ions, in particular $Bi^{+3}$ ions, for preventing and/or treating haemolytic uremic syndrome and, particularly, for preventing and/or treating infections caused by Shiga toxin-producing *Escherichia coli* strains.

Examples of Shiga toxin-producing *Escherichia coli* strains are, for example, but not limited to, strains O157:H7, 026:H11, O103:h2, O111:NM, O121:H19, and O145:NM.

Furthermore, a particular object of the invention is a method using a medicament containing bismuth ions for preventing and/or treating haemolytic uremic syndrome and, even more particularly, for preventing, propagating, reducing the excretion of and/or treating infections caused by Shiga toxin-producing *Escherichia coli* strains.

Preferably, the medicament is to be administered orally, although those with an average skill in the art will recognize, from the teachings included herein, that other forms of administration are also possible. Thus, a medicament according to the invention, may be administered to a patient by any suitable route of administration. Suitable routes of administration include, without limitation, oral, parenteral, transdermal, enteral, intra-abdominal routes, etc.

Within the scope of the present invention, it is contemplated that bismuth ions may be delivered in a medicament additionally comprising other therapeutically active compounds. Such therapeutically active compounds may be selected from, but not limited to, antibiotic compounds, antibacterial compounds, pectin or other compounds having activity as antidiarrheals.

As used in the present invention, the term "administer" and variants thereof (for example, "administration" of a compound) in relation to bismuth ions, means introducing such ions into the system of a patient in need of such treatment. When bismuth ions are provided in combination with one or more additional active agents (for example, another antidiarrheal or an antibiotic), "administration" and its variants should each be understood as including sequential or concurrent introduction of bismuth ions and other agents.

As used in the present invention, the term "patient" includes humans and other animals, particularly mammals and other organisms. Thus, the methods may be intended for human therapy as well as in veterinary applications. Accordingly, in one particular embodiment, the patient is a mammal. In another particular embodiment, the patient is a human.

Unless otherwise indicated, when used in the present invention, the terms "treat", "treating" and "treatment" make reference to an action that occurs while a patient is suffering from the specified disease or disorder, which reduces its severity, delays or reduces the progression of the disease or disorder, or that cures the disease or disorder.

Unless otherwise indicated, the terms "prevent", "preventing" and "prevention" make reference to an action that occurs before a patient begins to suffer from the specified disease or condition inhibiting or reducing the severity of said disease or condition. In other words, the terms encompass prophylaxis.

Unless otherwise indicated, a "prophylactically effective amount" of a compound is an amount sufficient to prevent a disease or condition, one or more of its associated symptoms or prevent recurrence thereof. A prophylactically effective amount of a compound means an amount of therapeutic agent, alone or in combination with other agents, which provides a prophylactic benefit in the prevention of the disease. The term "prophylactically effective amount" may encompass an amount improving overall prophylaxis or enhances prophylactic effectiveness of another prophylactic agent.

According to the present invention, bismuth ions may be administered in the form of pharmaceutically acceptable salts or bases. A "pharmaceutically acceptable salt" or "a pharmaceutically acceptable base" of Bismuth refers to a salt or a base which is pharmaceutically acceptable and has the desired pharmacological activity of the starting compound. It should be understood that pharmaceutically acceptable salts and bases are non-toxic. Additional information concerning suitable pharmaceutically acceptable salts and bases may be found in Remington's Pharmaceutical Sciences, $17^{th}$ ed., Mack Publishing Company, Easton, Pa., 1985, which is herein incorporated by reference. In a specially preferred embodiment, bismuth ions are present in the form of $Bi^{+3}$ ions In particular embodiments, bismuth may be administered in the form of bismuth oxide, bismuth subnitrate, bismuth subsalicylate, bismuth subcitrate, bismuth subgallate or bismuth hydroxide. In preferred embodiments of the invention, the bismuth ion is administered to a patient in need thereof in the form of bismuth hydroxide and, even more preferably, in the form of colloidal bismuth hydroxide gel. In a specially preferred embodiment, the bismuth ion is administered as a colloidal bismuth hydroxide gel.

In particularly preferred embodiments of the invention, the bismuth ion is administered to a patient as a part of commercially available pharmaceutical formulations such as Cream of Bismuth Chobet® and Bismuth Chobet®.

As used in the present invention, a "therapeutically effective amount" is an amount of bismuth ion which, when administered to a patient, treats the disease effectively. The amount of a compound of the invention which constitutes a "therapeutically effective amount" may vary depending on a series of factors, including activity, metabolic stability, excretion rate and duration of the action of the compound, the age, weight, general health, sex, diet and species of the patient, mode and timing of administration of the compound, concurrent administration of adjuvants or additional therapies and severity of the disease for which a therapeutic effect is sought. A therapeutically effective amount under a particular circumstance may be determined without undue experimentation. In preferred embodiments, acceptable doses range from 450 to 1800 mg administered orally every approximately 4 hours. As is known in the art, it may be necessary to make adjustments according to the age, weight, general health, sex, diet and species of the patient and the mode and timing of administration of the compound, the concurrent administration of adjuvants or therapeutically active additional ingredients and severity of the disease for which therapeutic effect is sought, and said doses may be readily determined by routine experimentation.

The bismuth ion may be administered to a patient in any acceptable solid, semi-solid, liquid or gaseous dosage form. Acceptable dosage forms include, but are not limited to, lozenges, capsules, solutions, aerosols, creams, emulsions, gases, gels, granules, liniments, lotions, suppositories, ointments, pastes, powders, suspensions, injectables, syrups, and tablets. In a preferred embodiment of the invention, the bismuth ion is administered to a patient in liquid form. In a particular embodiment, the liquid form is commercialized in the form of a suspension.

In a particularly preferred embodiment, the suspension contains as an active principle colloidal bismuth hydroxide gel (CBHG) corresponding to 3 g of bismuth per 100 ml of product. According to the invention, in particular embodiments, for example, said suspension may be administered, to adults and children over 12 years, in an amount ranging from about 30 to about 60 ml, every 4 to 6 hours. In children under 12 years of age, administration may comprise from about 15 to about 30 ml, every 4 to 6 hours. In infants, administration may comprise about 5 ml, every 4 to 6 hours. However, it should be understood that, according to the teachings of the present invention and at the physician's discretion, other doses and amounts could also be used.

In a particular embodiment for the treatment of HUS, bismuth is administered until the symptoms of diarrhea have disappeared.

In a particular embodiment for prophylaxis of an infection by Shiga-toxigenic *Escherichia coli* in animals, it is possible to administer, for example, 0.5 ml per kg of body weight, in a suspension containing as an active ingredient colloidal bismuth hydroxide gel corresponding to 3 grams per 100 ml of product, every 24 hours. Preferably, the animal to be treated is selected from bovine, porcine, ovine, caprine or equine herds. Similarly, edible birds could be treated by adjusting the formulation of bismuth hydroxide gel for that purpose.

According to the invention, the medicament may comprise bismuth ions alone, or such ions may be formulated together with conventional excipients, pharmaceutical carriers, adjuvants and/or other medicinal or pharmaceutical agents. Acceptable excipients include, but are not limited to, (a) anti-sticking agents, such as croscarmellose sodium, crosprovidone, sodium starch glycolate, microcrystalline cellulose, starch and talc; (b) binders, such as cellulose, gelatin, hydroxypropyl cellulose, lactose, polyethylene glycol, polyvinylpyrrolidone, sorbitol, starch and xylitol; (c) coatings, such as cellulose and shellac; (d) disintegrants, such as cellulose, polyvinylpyrrolidone, sodium carboxymethyl cellulose, methylcellulose, microcrystalline cellulose and sodium starch glycolate and starch; (e) bulking agents, such as calcium carbonate, cellulose, calcium dibasic phosphate and mannitol; (f) flavouring/perfuming agents; (g) colouring agents; (h) glidants, such as calcium stearate and colloidal silicon dioxide; (i) lubricants, such as calcium stearate, magnesium stearate, polyethylene glycol, and talc; (j) preservatives, such as citric acid, vitamin C and vitamin E. Pharmaceutical carriers include soluble polymers, natural or synthetic, insoluble or biodegradable polymeric microparticles, microcapsules, lipoproteins, liposomes, and micelles; and k) liquid media, such as water, glycerin, polyethylene glycol, and propylene glycol.

A pharmaceutical composition of the invention will contain a therapeutically effective amount of bismuth ion, wherein the remainder of the pharmaceutical composition comprises one or more pharmaceutically acceptable excipients. Generally, the bismuth ion will be present at a ratio of from 1% to 20% by volume of pharmaceutically acceptable composition, with the remainder of the pharmaceutical composition being made up of one or more pharmaceutically acceptable excipients. Typically, the bismuth ion will be present at a ratio of from 2% to 5% by weight of the acceptable composition, wherein the remainder of the pharmaceutical composition is made up of one or more pharmaceutically acceptable excipients. Methods for preparing the dosage forms of the invention are well-known, or will be apparent to those skilled in the art; for example, see Remington's Pharmaceutical Sciences, 18th Ed., (Mack Publishing Company, Easton, Pa., 1990).

A therapeutically effective amount of a compound of the invention will vary depending on a series of factors, including activity, metabolic stability, excretion rate and duration of the action of the compound, age, weight, general health, sex, diet, and the species of the patient, the mode and timing of administration of the compound, presence of adjuvants, of additional therapeutically active ingredients in the composition and the severity of the disease for which the therapeutic effect is sought.

The present inventors have also found that Shiga-toxigenic Escherichia coli O157:H7 is sensitive to treatment with the usual doses of CBHG.

Furthermore, it was found that CBHG is capable of attaching to Shiga-toxigenic Escherichia coli O157:H7 and then removing it by slight centrifugation. There is a direct relationship between bacterial strain virulence and its ability to adhere to the walls of the gastrointestinal epithelium. Thus, according to the results, and without wishing to be bound to any particular theory it may be said that this ability of CBHG to capture and promote dragging away of bacteria hinders bacterial adherence to the gastrointestinal epithelium and colony formation. Considering that CBHG does not reduce gastrointestinal motility, mechanic fixation to bismuth should also favour a rapid excretion of Shiga-toxigenic Escherichia coli O157:H7 from the gastrointestinal tract.

In order to develop HUS in a patient, it is necessary for the Escherichia coli strain to have Shiga-toxigenic capacity, since the Stx cytotoxin is the major pathogenicity mechanism of STEC and its synthesis is related to the presence of the STX bacteriophage, which is inserted within the genome. The results obtained by the present inventors, show a significant decrease in cytotoxic activity on Vero cells at sub-inhibitory and sub-clinic concentrations of CBHG. Quantification of toxins by immunoabsorption did not show significant differences from controls. Accordingly, and without wishing to be bound to any particular theory, it is suggested that a decrease in Stx activity is a result of a direct interaction of CBHG with the activity of the toxins in eukaryotic cells.

Stx activity is directly related to the enzymatic function of the cytotoxic subunit A. Even when it is known that some compounds may act as neutralizers in the binding process of the toxin to its receptor, thereby generating inhibition of cytotoxicity on Vero cells (Gamage et al., *J Bacteriol* 186, 5506-5512, 2004), and without wishing to be bound to any particular theory, the present inventors suggest that this effect may be related to the fixation of bismuth on one or various cysteine-rich Stx sites involved in cytotoxicity. Experimental data coincide in proving that the effects of bismuth are based on the inhibition by the $Bi^{3+}$ cation of enzymatic activities of microbial proteins rich in cysteine residues. $Bi^{3+}$ binds strongly to a protein through formation of Bi—S bridges displacing other cations involved in the function of the proteins in question.

The results achieved in trials measuring the effect on free 933W phage are highly promising; CBHG reduces phage titer in up to 80 and 90%. Stx damages endothelial and tubular renal cells, which is why they are considered as major virulence factors (Williams et al., 1999). Stx1 and 2 are encoded in lamboid pro-phage genome, and may be induced by different stimuli such as UV light or mitomycin C. As a result of induction, bacterial host cells are lysed and release phage particles, thus infecting other neighboring cells or are released into the environment, remaining as potential carriers of virulence genes. These phages, inserted within the bacterial genome, encode Shiga toxin production and are responsible for disseminating these virulence factors onto other virulent bacteria.

In the examples included below, studies were carried out using colloidal bismuth hydroxide gel. This very simple chemical entity, in an aqueous media, can only release bismuth ions and OH⁻ radicals. It is clear that in the compound used in the examples, the bismuth ion exposed in the test media is the only active chemical entity. The OH group of CBHG in the aqueous assay medium and in cellular interphases lacks therapeutic action and significance. For this reason, it may be said that the presence of a bismuth ion is responsible for the results achieved in the tests. By extrapolation, any bismuth compound providing this ion to the medium should produce the same activity and effects.

The results obtained by the present inventors show that CBHG has an inhibitory action on the cytotoxic activity of Shiga toxins. Considering the CBHG concentration currently used in diarrhea therapeutics, as an antidiarrheal and as a gastrointestinal mucus protector (30 mg/mL), it may be affirmed that Shiga-toxigenic Escherichia coli O157:H7 is sensitive to the usual doses of CBHG.

It has also been demonstrated that CBHG significantly inhibits replication of free bacteriophage, which is responsible of the virulence of Escherichia coli O157:H7. These phages, inserted within the bacterial genome, encode Shiga toxin production and are responsible of disseminating the ability to produce these virulence factors in other non-virulent bacteria. Therefore CBHG may be a powerful tool for preventing dissemination of Stx-producing strains, in human as well as in animal reservoirs.

According to the results, and without wishing to be bound to any particular theory, it may be suggested that this ability of CBHG to fix and promote bacterial dragging, by hindering bacterial adherence to the gastrointestinal epithelium, would prevent bacterial colony buildup. Considering that CBHG does not reduce gastrointestinal motility, mechanic fixation to bismuth should further favour a rapid excretion of Shiga-toxigenic Escherichia coli O157:H7 out of the gastrointestinal tract.

The examples included below are presented for the only purpose of providing particular embodiments of the invention and should not be construed as limiting their scope.

EXAMPLES

Determination of Sensitivity to Bismuth Ions

Minimum inhibitory concentration (MIC) is the most frequently used elective indicator in antimicrobial therapy. Therefore, the MIC value of colloidal bismuth hydroxide gel (CBHG) was determined for Shiga-toxigenic Escherichia coli O157:H7. In this essay, $1/50$, $1/25$, $1/15$, $1/10$, $1/5$, and $1/3$ dilutions were used, corresponding to the following bismuth concentrations: 0,6 mg/mL, 1,2 mg/mL, 2 mg/mL, 3 mg/mL, 6 mg/mL, and 10 mg/mL.

As a result, a MIC corresponding to 10 mg/mL of bismuth was obtained for Shiga-toxigenic Escherichia coli O157:H7. MIC values were in the order of $Bi^{+3}$ concentrations of 10 mg/mL.

Determination of Bacterial Fixation to a Bismuth Suspension

Bacterial cultures of Shiga-toxigenic Escherichia coli O157:H7 were adjusted to 0,5 McFarland. The Bismuth ($Bi^{+3}$) compound was added to the culture (2 mg/mL, sub-inhibitory concentration) and the suspension was incubated at 37° C., under stirring. Subsequently samples were collected, at specific periods of time (5, 24, and 168 hr), in order to determine the total number of viable microorganisms, while other samples were centrifuged at 1000 rpm for 5 min. Remnant bacteria in the supernatant were considered as not fixed and counted on agar plates (Sox and Olson, 1989). The number of fixed bacteria was obtained by subtracting the number of not fixed bacteria from total viable bacteria. As a result, it was determined that bacterial fixation to CBHG for Shiga-toxigenic *Escherichia coli* O157:H7 comprised from 90 and 98%.

Effect on Shiga Toxins

Various techniques for evaluating Shiga toxin expression were used. *E. coli* O157:H7 EDL933 strain was grown in LB broth, at 37° C. and for 18 hr, under stirring. The bacterial culture was fractionated into 200 µl aliquots, in 5 ml of LB broth supplemented with test compounds (CBHG dilutions of 1/5 and 1/3, corresponding bismuth concentrations of 6 mg/mL and 10 mg/mL) and further incubated for 18 hr, at 37° C., under stirring at 140 rpm. Positive drug-free controls, negative controls without bacterial culture for each drug and concentration, and a double negative control without drug or bacterial culture were used. Cultures were centrifuged at 8000 rpm for 10 min at 4° C., supernatants were removed and filtered through a 0.43 µm membrane. They were then stored at −20° C. and used in the following tests:

Cytotoxicity Assay:

A 96-well microplate procedure was used, seeded by co-culture of Vero cells with samples. Vero cells were grown in Sigma 0643 MEM (Minimum Essential Medium) (with 200 mg/l streptomycin and 100 mg/l penicillin) spiked with 10% foetal calf serum (FCS), at 37° C., with 5% $CO_2$. Cells were picked in trypsin and transferred to MEM without FCS. 200 µl samples of pure supernatant from bacterial cultures were seeded in the first row and 2× dilutions were made using MEM with 15% FCS (1, ½, ¼, ⅛, ¹⁄₁₆) in each column. Each column was seeded with drug-treated samples at different concentrations. Then 100 µl of a $2.5 \cdot 10^6$ cells/mL suspension was inoculated in each well containing samples. The microplates were incubated in an oven at 37° C. with 5% $CO_2$ and readings were made for 48 hr at 12 hour intervals, by inverted microscopy. After 48 hr cytotoxic activity titers were determined. Cytotoxic activity titers at 50% (DC50) were determined by dilution. Cells were stained and fixed with a solution of 0.75% Crystal Violet in 40% methanol and photographs were taken.

Determination of Stx Concentration by Immunoenzymatic Analysis:

A RIDASCREEN® Verotoxin test (R-Biopharm Latinoamérica S.A.), an enzyme-linked immunoabsorbent assay (ELISA), was used for detecting Shigatoxin 1 and 2 (Stx-I and Stx-II). Supernatants of bacterial cultures treated with bismuth drugs were tested for extracellular Stx. Measurements were made photometrically at a wavelength of 450 nm. As a result, a significant decrease of active Stx toxin titers was observed in samples treated with a ⅕ dilution of CBHG, which corresponds to bismuth concentrations of 6 mg/mL. No significant (p=0.6849) differences were observed between treated supernatants and untreated control at the assessed dilutions.

Effect on Free 933W Phage

The effect of CBHG on 933W lambda phage encoding Stx toxin was analyzed. The phage solution was titered and incubated with the compounds in four different dilutions, ¹⁄₂₄; ¹⁄₁₂; ⅙, and ⅓, which correspond to bismuth concentrations of 1.25 mg/mL, 2.5 mg/mL, 5 mg/mL and 10 mg/mL, for 24 hours, at 37° C. under constant stirring. Then, the presence of phages was observed using the double layer agar method and *E. coli* DH5α as a receptor strain. The number of formed lysis plaques was counted and their effect was evaluated.

As for the effect of the CBHG Stx 933W encoding phage, a statistically significant (p<0.05) decrease in CBHG-treated phage titer was observed, as compared to non-treated phage. There was a 90% decrease in the amount of phage for a CBHG dilution of ⅓, which corresponds to a bismuth ion concentration of 10 mg/mL and 86% for a CBHG dilution of ⅙, which corresponds to a bismuth ion concentration of 5 mg/mL.

| Shiga-toxigenic *Escherichia coli* | % fixed CFU Colloidal bismuth hydroxide gel 2 mg/mL |
|---|---|
| 6 hs | 89.60% |
| 24 hs | 94.10% |
| 168 hs | 97.70% |

Percentage of Shiga-Toxigenic *Escherichia coli* Fixation to CBHG

Effect of CBHG on Shiga Toxins in Vero Cells, Expressed as Percentages of Cytotoxicity.

| Dilution of toxin extract | Colloidal bismuth hydroxide gel | | Control without drug | |
|---|---|---|---|---|
| | 3 mg/mL | 6 mg/mL | 3 mg/mL | |
| ½ | 50% | 10% | 80% | 80% |
| ¼ | 20% | — | 80% | 80% |
| ⅛ | — | — | 60% | 50% |
| ¹⁄₁₆ | — | — | 50% | 20% |
| ¹⁄₃₂ | — | — | — | — |

Effect of the Drug on 933W Phage Encoding Stx Toxin

| Bismuth concentration | Bacterio933W phage PFU/mL | Percentage of phage titer decrease (%) |
|---|---|---|
| 0 | 394 ± 21 | |
| | Colloidal bismuth hydroxide gel | |
| 1.25 | 93 ± 25^ | 76 |
| 2.5 | 74 ± 13^ | 80 |
| 5 | 48 ± 5^ | 86 |
| 10 | 38 ± 6^ | 90 |

Results were expressed as the mean ± standard deviation of 5 experiments.
^p < 0.001.

The invention claimed is:

1. A method for treating a disease wherein the disease is an infection caused by at least one strain of Shiga toxin-producing *Escherichia coli*, the method comprising orally administering a pharmaceutical composition comprising a bismuth ion to a patient in need thereof.

2. The method of claim 1, wherein the disease is haemolytic uremic syndrome.

3. The method of claim 1, wherein said at least one strain of Shiga toxin-producing *Escherichia coli* is selected from the group consisting of *Escherichia coli* strains O157:H7, O26:H11, O103:h2, O104:H4, O111:NM, O121:H19, and O145:NM.

4. The method of claim 1, wherein the bismuth ion is selected from the group consisting of a bismuth ion forming a pharmaceutically acceptable salt and a bismuth ion forming a pharmaceutically acceptable base.

5. The method of claims 1, wherein the bismuth ion is in a form selected from the group consisting of bismuth oxide, bismuth subnitrate, bismuth subsalicylate, bismuth salicylate, bismuth subcitrate, bismuth subgallate, bismuth hydroxide and bismuth subcarbonate.

6. The method of claim 1, wherein the bismuth ion is $Bi^{+3}$.

7. The method of claim 6, wherein the bismuth ion is in a form selected from the group consisting of bismuth hydroxide and colloidal bismuth hydroxide gel.

8. The method of claim 6, wherein the $Bi^{+3}$ ion is included in a medicament in the amount of from about 1% to about 20% by volume of the total volume of the medicament.

\* \* \* \* \*